(12) United States Patent
Abdelrahman

(10) Patent No.: US 7,229,828 B2
(45) Date of Patent: Jun. 12, 2007

(54) SUGAR CANE PRODUCTION

(76) Inventor: Layla Zakaria Abdelrahman, 8 Beaver Road, Didsbury, Manchester, M20 6SR (GB)

( * ) Notice: Subject to any disclaimer, the term of this patent is extended or adjusted under 35 U.S.C. 154(b) by 33 days.

(21) Appl. No.: 10/365,835

(22) Filed: Feb. 13, 2003

(65) Prior Publication Data

US 2003/0219896 A1    Nov. 27, 2003

Related U.S. Application Data

(63) Continuation-in-part of application No. 09/377,941, filed on Aug. 20, 1999, now Pat. No. 6,521,452.

(51) Int. Cl.
*C12N 5/00*    (2006.01)
*C12N 5/02*    (2006.01)

(52) U.S. Cl. ..................................... 435/410

(58) Field of Classification Search ............... 435/420, 435/410
See application file for complete search history.

(56) References Cited

U.S. PATENT DOCUMENTS

| | | | |
|---|---|---|---|
| 4,562,663 A | 1/1986 | Redenbaugh | 47/58 |
| 5,108,775 A * | 4/1992 | Bousser | 426/616 |
| 5,427,593 A | 6/1995 | Carlson et al. | 47/57.6 |

OTHER PUBLICATIONS

Characterization of molybdenum deficiency in sugar-cane. J.E. Bowen The journal of the faculty of agriculture University Of the West Indies. 56(3) 185-288 (1979).*
R.L.M. Pierik, In Vitro Culture of Higher Plants. 1997 Kluwer Academic Publishers.*
Kilby et al., Plant Cell, Tissue and Organ Culture 28: 275-280. 1992.*
*Plant Cell Biotechnology*, Endress, R., ed., Springer-Verlag (Berlin: 1994), p. 110.
C.H. Bornman in *Synseeds*, Redenbough, K., ed., Chapter 6 "Maturation Of Somatic Embryos", CRC Press (Boca Raton: 1993), p. 105-113.

Taylor et al., "Establishment of Embryonic Callus and High Protoplast Yielding Suspension Cultures of Sugarcane," *Plant Cell, Tissue and Organ Culture*, 28:69-78 (1992).
*Plant Biochemistry*, P.M. Dey & J.B. Harborne, eds., Academic Press (San Diego, California: 1997), Chapter 15.2 "Plant Cell Culture", at pp. 518-519.
*Glossary of Plant Tissue Culture*, Donnelly, D.J. and Vidaver, W.E., Belhaven Press (London: 1988), p. 15.
J.J. Finer, Chapter 5 "Plant Regeneration via Embryogenic Suspension Cultures," in *Plant Cell Culture: A Practical Approach*, Dixon, R.A. and Gonzales, R.A., eds., Oxford University Press, (Oxford: 1994), p. 110-112.
I.K. Vasil, "Somatic Embryogenesis and its Consequences in the Gramineae," in *Tissue Culture in Forestry and Agriculture*, Henke, R. et al., eds., Plenum Press (New York: 1984), pp. 31-47.
B.S. Ahloowalia & A. Maretzki, "Plant Regeneration Via Somatic Embryogenesis in Sugarcane," in *Plant Cell Reports*, (Hawaii: 1983), pp. 21-25.
Wai-Jane Ho & J.K. Vasil, "Somatic Embryogenesis in Sugarcane (Saccharum officinarum L.): Growth and Plant Regeneration from Embryogenic Cell Suspension Cultures," *Annals of Botany Company*, (Florida: 1983), pp. 719-726.
Publication: Frank Blackburn, Tropical Agriculture Series, "Sugarcane", Published in the United States of America by Longman Inc., New York (1984).

* cited by examiner

*Primary Examiner*—Anne Kubelik
*Assistant Examiner*—Annette Para
(74) *Attorney, Agent, or Firm*—Welsh & Katz, Ltd.; Thomas W. Tolpin

(57) ABSTRACT

Plants, particularly sugar cane plants, are reproduced using explant material which may be derived from leaves, shoots, roots and other plant parts. Somatic embryos are produced by culturing immature embryos from the explant material and then culturing mature, somatic embryos from the immature embryos. All achieved in liquid suspension culture, which allows micro propagation of sugar cane without the culture suffering, browning at any stage. The mature embryos can then be encapsulated to form artificial seeds for germination purposes.

9 Claims, No Drawings

SUGAR CANE PRODUCTION

RELATED APPLICATIONS

This application is a continuation-in-part of U.S. Pat. No. 6,521,452, issued Feb. 18, 2003, application Ser. No. 09/377,941, filed Aug. 20, 1999 entitled "Sugar Cane Production" before Examiner Anne M. Grumberg in Group Art Unit 1661, which is based upon priority International Application PCT/GB98/00387 filed Feb. 20, 1998, International Publication No. WO 98/37173 published Aug. 27, 1998, which is based upon British Application 9703628.9 filed Feb. 21, 1997.

BACKGROUND OF THE INVENTION

The present invention relates to a method of plant cell culture. In particular, the present invention relates to a method for reducing browning of a plant cell culture.

The phenomenon of 'browning' is a significant problem encountered in the in vitro culture of plant cells. Browning (or sometimes 'blackening') of cultured plant material occurs when phenolic substances, such as tannins or other hydroxyphenols, are oxidised to highly active quinone compounds which then cyclise, polymerise and/or oxidise proteins to form increasingly melanic compounds. The result of this is that the plant tissue becomes brown or black and growth of the plant cells in culture is inhibited, frequently irreparably. Thus, browning represents a serious obstacle to the successful growth of plant cells in culture.

Browning has been observed in a wide range of plant explants and plant cell cultures and in particular in tropical species, which often contain high levels of phenolic substances.

A number of approaches have been taken in attempting to address the problem of browning. These include the addition of anti-oxidants, such as ascorbic acid, and chelating agents, such a EDTA, and the use of activated charcoal to absorb inhibitory phenolic compounds. However, no single approach has proved satisfactory, and it has frequently been necessary to combine several of these techniques. A drawback of the use of activated charcoal is that as well as absorbing problematic phenolic compounds, it may also absorb growth factors or other mediators added to the culture medium and therefore higher amounts of the growth factors or other mediators must be added. Even in combination, the previously adopted techniques have often failed to control browning in plant cell cultures.

One plant known to suffer from browning in culture is the commercially important crop plant, sugar cane. Sugar cane is a perennial tropical grass with tall unbranched stems or canes from which sugar is extracted. The sugar cane stem is roughly circular or oval in cross-section, and comprises a series of joints each of which in turn comprises a node and an internode. Each node comprises of a lateral bud in an axial leaf, a band containing root primordia, and a growth ring.

In commercial production, sugar cane is usually grown from stem cuttings (or 'setts'), each of which generally has at least two buds. The buds develop to form primary stems, the basal buds of which in turn develop into secondary stems, from which tertiary stems may develop, and so on.

Sugar cane roots may develop either from the root primordia of a cutting itself or from the root primordia of stem shoots developing from the cutting, each of which produce their own root system. Roots developing from the primordia of the sugar cane stem cutting tend to be thin and branched. Those formed by the root primordia of new stem shoots tend to be thicker and less branched. Sugar cane stem cuttings may be rooted in water or an aqueous medium. It has been reported that sugar cane roots can develop at temperatures as low as around 10° C.

BRIEF SUMMARY OF INVENTION

An object of the present invention is to address the significant problem of browning in plant cell cultures.

According to one aspect of the present invention there is provided a method of reducing browning of a plant cell culture, comprising introducing into said plant cell culture a mucilaginous material obtained from sugar cane material by at least partially submerging said sugar cane material in an aqueous medium.

The present invention provides a method for plant cell culture in which the browning is controlled, improving the growth of the cultured plant cells. The method of the present invention is applicable to a wide range of plants and cell types, since browning is a widespread problem in plant cell culture.

Preferably, the sugar cane material comprises sugar cane root material, although other parts of the plant may be used. For example, the mucilaginous material may be obtained from a root zone of a sugar cane plant before emergence of a root, or from internodes, in particular very young internodes. It will be appreciated, therefore, that the mucilaginous material may be obtained from sugar cane material of almost any size and composition.

The mucilaginous material may be obtained by at least partial submersion of the sugar cane material in any suitable aqueous medium, including commercially available culture media and solutions. Advantageously, however, the mucilaginous material may be obtained by at least partial submersion of the sugar cane root material in water. This is clearly of economic benefit.

In the case where the mucilaginous material is obtained from sugar cane root material, the sugar cane material should preferably be submerged sufficiently to cover the root material in the aqueous medium.

The mucilaginous material can be produced with a young whole sugar cane plant which is still undergoing rooting process. This is possible by supporting the plant to allow the roots only to be submerged in aqueous solution.

The mucilaginous material can be produced even if the whole cutting is totally submerged, but partial submersion is better since it allows more roots to grow.

The temperature of the aqueous medium may be controlled in order to achieve optimum production of the mucilaginous material. The temperature of the aqueous medium is preferably within the range of from around 20° C. to around 50° C., since it has been found that production of the mucilaginous material by submerged sugar cane roots is poor at temperatures of below 20° C. or above 50° C. More preferably, the temperature of the aqueous medium is within the range of from around 25° C. to around 35° C.

The sugar cane material may be incubated to form the mucilaginous material for a period of 2 to 6 weeks. In a particularly preferred embodiment the period is one month, this being sufficient to give a useful amount of material.

The production of the mucilaginous material can continue e.g. as long as new roots are produced when using root-forming sugar cane material. The mentioned practical limit of one month applies where growth occurs only in distilled water whereby root growth may stop after this period. Where large scale production is required, the roots could be induced to grow in a tank while the shoot is growing. The sugar cane could thereby produce a massive root system which means more mucilage.

The activity of the mucilaginous material is substantially resistant to autoclaving, and the materially may therefore usefully be autoclaved to provide a sterile preparation for introduction into plant cell cultures. Any conventional autoclaving technique may be adopted.

Alternatively, the mucilaginous material may be extracted into alcohol, such as ethanol. Preferably, absolute alcohol is used. It has been found that when mucilaginous material is extracted into ethanol and the ethanol is subsequently allowed to completely evaporate, the residual material is of a waxy appearance.

Advantageously, in the case where the mucilaginous material is obtained from sugar cane material comprising root material, root material coated in the viscous mucilaginous material may be cut away from the sugar cane stem and the mucilaginous material then extracted from the cut root material. In this way, the sugar cane stem may be put to further use.

The mucilaginous material may be introduced into the plant cell culture at any effective concentration. It will be appreciated that this may vary depending upon the plant and cell type being cultured. By way of example, the mucilaginous material may be used in an amount corresponding to the amount of mucilaginous material produced by one or two nodes of rooted sugar cane material per litre of culture medium.

The method of the invention may be used to reduce browning of all types of plant cell cultures. For instance, the method has been shown to be effective in reducing browning in explants, callus cultures and liquid suspension cultures. The mucilaginous material may be introduced into the plant cell culture at any stage where browning presents a problem. The mucilaginous material may be introduced or incorporated into any liquid culture medium or into or onto any solid culture medium. The range of culture media used in plant cell culture and the particular media suitable for culture of specific plant and cell types are known in the art.

A further aspect of the present invention provides a preparation for reducing browning of a plant cell culture, said preparation comprising a mucilaginous material obtained from sugar cane material by at least partially submerging said sugar cane material in an aqueous medium.

A still further aspect of the present invention provides a plant cell culture containing a preparation comprising a mucilaginous material obtained from sugar cane material by at least partially submerging said sugar cane material in an aqueous medium.

A more detailed explanation of the invention is provided in the following description and appended claims.

DETAILED DESCRIPTION OF THE INVENTION

A detailed description of the preferred embodiments and best modes of practicing the invention are described therein.

The invention will now be described in the following non-limiting examples.

EXAMPLES

Production of Mucilaginous Material

Sugar cane setts rooted in distilled water were incubated in distilled water at 35° C. for one month. After this time, the mucilaginous material produced by the sugar cane material was extracted by dissolving in absolute alcohol.

Anti-Browning Activity of Mucilaginous Material

The mucilaginous material was tested using a range of plants known to be susceptible to browning in culture. Sugar cane, date palm, bamboo and banana were chosen as representative examples of such plants. The mucilaginous material was added to explant (sugar cane, date palm and bamboo), callus cultures (sugar cane, date palm, bamboo and banana) and suspension cultures and liquid embryogenic cultures (sugar cane, date palm, bamboo and banana) and its ability to control browning in these cultures was observed. Explants comprised leaf explants, since leaves tend to be most affected by browning when wounded. The mucilaginous material was added to culture media at a concentration corresponding to the product of one sugar cane node per litre. For cultures grown on solid media, the mucilaginous material was incorporated into a liquid medium which was poured on top of the solid media to form a double layer. Alternatively it can be incorporated in the solid media before solidification.

Preparation of Explant from Sugar Cane

Sugar cane setts were immersed in a water bath at 52° C. for 2 days to expose any contamination and to promote shooting. The setts were subsequently grown on regularly fertilised compost at 25° C. with a 16 hour light photoperiod in a glasshouse from November to April and using natural daylight from May to October. Leaf explants were excised at three months as 5 mm segments of outer and inner leaves. The sugar cane leaf explants were sterilised by soaking in 95% ethanol for 20 minutes.

Preparation of Explant from Date Palm

Date palm seeds were washed under running water for 5 minutes, before being placed in 2% sodium hypochlorite solution for 20 minutes. The seeds were then washed 3-4 times in sterile water and placed on sterile tissue paper to dry under laminar flow. The seeds were then immersed in 90% alcohol and flamed, and placed on damp tissues or damp filter paper inside a petri dish. The petri dish was sealed and the culture incubated at 27° C. under a cycle of 8 hours of light, 16 hours dark. After one week, the resultant shoot was excised.

Preparation of Explant from Bamboo

An ornamental bamboo plant was grown in liquid culture. The auxiliary shoots were removed and sterilised in 2% sodium hypochlorite for 20 minutes. The shoots were then washed 3 times using distilled water.

Preparation of Explant from Banana

The bases of leaf sheaths were isolated from a small plant or sucker. The cut ends were waxed, sterilised in 2% sodium hypochlorite solution and washed 3 times in distilled water.

The waxed part was removed and the leaves cut into small fragments about 3 mm long and placed in solid or liquid culture medium. The culture was incubated either in dark or light and was shaken at 100 rpm.

Cell Culture Using Murashige and Skoog (MS) Culture Media

The basic culture medium was prepared from stock solutions and then supplemented with various combinations of plant growth regulators, vitamins and sugars, as required. Myoinositol, solidifying agent (agar) and carbohydrates were added to the media during preparation, as required. Culture media were made up using double distilled water. Heat-stable plant growth regulators as well as other compounds were added before autoclaving, while any heat labile compounds were added to the lukewarm media just prior to pouring into sterile plates. All media were adjusted to pH 5.8 using 1M NaOH or 1M HCl prior to autoclaving. In the case of solid media, 0.9% agar was added before adjustment of the pH. 3% sucrose was added to the media. Adjustments were made to the media, as required, depending upon the plant and cell type grown.

Callus and Suspension Cultures

Callus cultures were established by culturing explants in 90 mm×15 mm sterile plastic petri dishes containing MS medium solidified with 0.9% agar and containing 3 mg/l 2,4-dichlorophenoxyacetic acid (2,4-D). The petri dishes were sealed using parafilm to reduce water loss.

Suspension cultures were initiated by placing 05.-1.0 g (fresh weight) of callus material into sterile 250 ml Erlenmeyer shake flasks containing 50 ml of MS medium. The flasks were sealed with sterile aluminium foil and placed on rotary shakers at 100 rpm.

Results

The mucilaginous material was found to be effective in controlling browning of the callus and suspension cultures tested. In the absence of the mucilaginous material, browning was noted and growth of the plant material was inhibited.

The mucilaginous material was also found to be effective with explant material. By way of example, mucilaginous root material was used after being sterilised. Explants from sugar cane, banana, bamboo were immersed in this material for one week. All explants were found to be well preserved and no browning at all was seen.

Explant Growth

Parent U.S. application Ser. No. 09/377,941, of which this application is a continuation-in-part, describes explant growth and reference is made to that application for further details.

Various methods of breaking down plant tissue by homogenisation to provide multiple explants have been used for micropropagation in order to reduce the labour cost, e.g. ferns. Machine homogenisation is useful but can be very harmful for an explant which produces phenolic compounds due to browning. Experiments were conducted using the sugar mucilage material as follows:

Aseptic leaves of banana weighing about 4 g were placed in a sterile blender with 40 ml sterile MS shoot multiplication medium and root mucilage. The mixture was blended for 2 seconds. 10 ml aliquot was aseptically transferred into a 10 ml culture container with 10 ml solid MS shoot multiplication medium and shaken at 100 rpm under continuous light conditions.

No oxidation was observed, and the culture produced healthy shoots within one month.

This mucilage material could be used not only for somatic embryogenesis but for large scale micropropagation for shoot production.

As mentioned in the parent application, abscissic acid (ABA) is useful. ABA with an auxin (depending on the kind of plant material) with root mucilage provides a medium which can be used for any plant for successful callus and embryogenic suspension. Since ABA stops the growth of non-embryogenic cells and the mucilage controls the browning, good results can be obtained.

Non-embryogenic cells can also be controlled either by cold storage or heat treatment or agitation at 500 rpm.

Embryos can be encapsulated prior to germination as with sugar cane as described in the parent application.

The invention is not intended to be restricted to the above examples, which are included by way of illustration only.

Although embodiments and examples of the invention have been shown and described, it is to be understood that various modifications and substitutions, as well as rearrangements of method steps, parts, components, equipment, apparatus, plants and cells types, can be made by those skilled in the art without departing from the novel spirit and scope of this invention.

What is claimed is:

1. A method of reducing browning of a plant cell culture, comprising introducing into said plant cell culture a mucilaginous material obtained from sugar cane material by at least partially submerging said sugar cane material in an aqueous medium.

2. A method according to claim 1, wherein the sugar cane material comprises sugar cane root material.

3. A method according to claim 1, wherein the aqueous medium is water.

4. A method according to claim 1, wherein the temperature of the aqueous medium is between from around 20° C. to around 50° C.

5. A method according to claim 4, wherein the temperature of the aqueous medium is between from around 25° C. to around 35° C.

6. A method according to claim 1, wherein the mucilaginous material comprises autoclaved mucilaginous material.

7. A method according to claim 1, wherein the mucilaginous material comprises mucilaginous material extracted into alcohol.

8. A method according to claim 1, wherein the plant cell culture comprises a culture selected from explant, callus and suspension and embryogenic liquid cultures.

9. A preparation for cell material treatment comprising a mucilaginous material, obtained from sugar cane material by at least partially submerging said sugar cane material in an aqueous medium, in combination with ABA (abscissic acid).

* * * * *